United States Patent

Caron et al.

[11] Patent Number: 5,735,854
[45] Date of Patent: Apr. 7, 1998

[54] DEVICE FOR APPLYING A SCREW

[76] Inventors: Philippe Caron, Boulevard Daunou, 62200 Boulogne Sur Mer; Jacques Chereau, 2, rue Marie Curie, 44470 Carquefou, both of France

[21] Appl. No.: 716,639

[22] Filed: Sep. 13, 1996

[30] Foreign Application Priority Data

Apr. 12, 1996 [EP] European Pat. Off. ............ 96440028

[51] Int. Cl.⁶ .................................................. A61B 17/56
[52] U.S. Cl. ................... 606/73; 606/104; 81/177.4; 81/467
[58] Field of Search .................. 606/104, 73, 72, 606/60, 86, 102; 81/177.4, 490, 488, 57.37, 467; 206/338, 339

[56] References Cited

U.S. PATENT DOCUMENTS

| | | | |
|---|---|---|---|
| 2,248,054 | 6/1941 | Becker | 606/104 |
| 3,892,232 | 7/1975 | Neufeld | 606/104 |
| 4,936,169 | 6/1990 | Parsons | 81/57.37 |
| 4,998,452 | 3/1991 | Blum | 81/57.37 |
| 5,031,489 | 7/1991 | Young et al. | 81/430 |
| 5,199,331 | 4/1993 | Tsukamoto | |
| 5,231,902 | 8/1993 | Uno et al. | 81/57.44 |
| 5,396,819 | 3/1995 | Bradley . | |
| 5,445,641 | 8/1995 | Frigg et al. . | |
| 5,531,143 | 7/1996 | Habermehl et al. | 81/438 |
| 5,584,221 | 12/1996 | Petrantoni | 81/434 |

FOREIGN PATENT DOCUMENTS

| | | |
|---|---|---|
| 512262 | 11/1992 | European Pat. Off. . |
| 668187 | 7/1929 | France . |
| 3816718 | 11/1989 | Germany . |
| 260155 | 2/1949 | Switzerland . |
| 659607 | 10/1951 | United Kingdom . |
| 26471 | 11/1994 | WIPO . |

*Primary Examiner*—Guy V. Tucker
*Attorney, Agent, or Firm*—Ostrolenk, Faber, Gerb & Soffen, LLP

[57] ABSTRACT

Screwing device which incorporates a screw charger. The device comprises a tube which encloses axially aligned screws and which is capable of being made integral with a maneuvering shaft. The tube comprises, at its free end, rings for blocking the head of a screw and allowing only the threaded part of the screw to protrude. The screw is brought into this position with the aid of an axial thrust shaft which can be maneuvered by the user. For rotationally blocking the screw in the screwing position, the tube comprises at least two longitudinal slots which confer on the free end a certain transverse elasticity permitting a screw to be brought into the screwing position, and ensure that the screw is not driven in rotation and is released when the limit torque is reached.

4 Claims, 2 Drawing Sheets

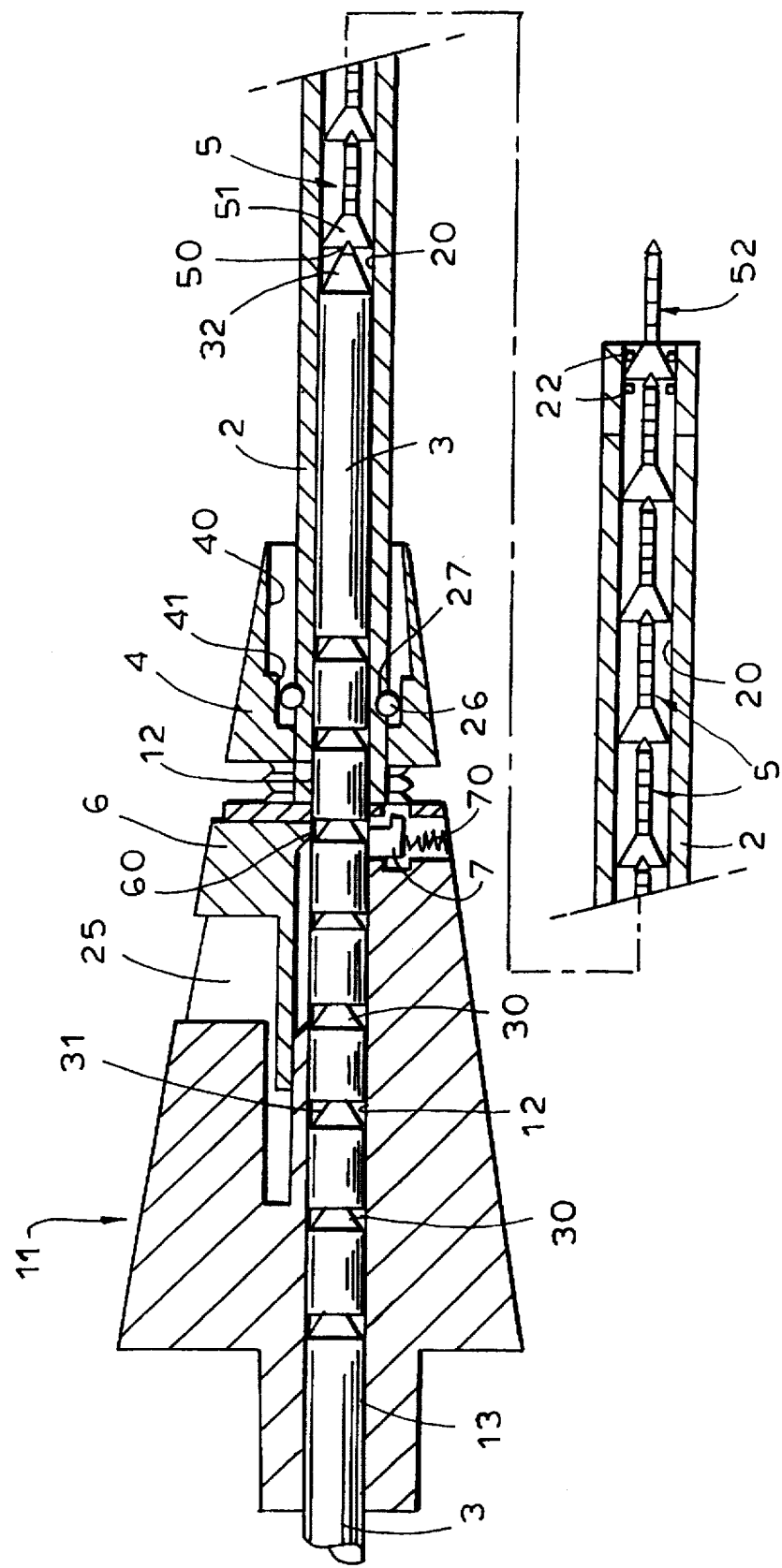

DEVICE FOR APPLYING A SCREW

BACKGROUND OF THE INVENTION

The present invention relates to a screwing device which incorporates a screw charger and which can be used particularly in the field of maxillofacial surgery, and which is especially intended to facilitate the screwing of osteotomy plates.

Screwing devices are already known which include a casing for storage of screws, which screws are removed by the user, upon each application, with a screwing instrument which for this purpose has, at its end, a means for gripping the screw head, and which is equipped with a system for limiting the clamping torque.

However, these devices compel the user to remove a new screw from a storage casing upon each application and, prior to the screwing operation, to adjust the system for limiting the clamping torque as a function of the type of screw.

SUMMARY OF THE INVENTION

The object of the present invention is to remedy these disadvantages by proposing a screwing device with charger which does not require adjustment of the clamping torque and which allows the user to benefit from a plurality of screws which are immediately available one after the other in the screwing position at the end of the screwing instrument.

The screwing device with charger which is the subject of the present application is characterized essentially in that it comprises a tube which encloses axially aligned screws and which is capable of being made integral with a maneuvering shaft, said tube comprising, at its free end, on the one hand a means for blocking a screw head and allowing only the threaded part of said screw to protrude, which screw is then situated in the screwing position and is immobilized in terms of rearward and forward displacement, said screw being brought into this position with the aid of an axial thrust means which can be maneuvered by the user, and, on the other hand, a means for rotationally blocking the screw in the screwing position; said tube also comprising, at its free end, at least two longitudinal slots which confer on said free end a certain transverse elasticity which means that the screw brought into the screwing position can no longer be driven in rotation when the limit torque is reached, and which additionally permits its release on completion of the operation.

According to one characteristic of the invention, the means for blocking the screw nearest the free end in the screwing position consists of two annular and coaxial projections which are spaced apart from one another and between which the head of said screw takes up position, which arrangement prevents it from leaving the tube and from falling back during screwing.

According to another characteristic of the invention, the thrust means for the screws in the tube is a rod which axially traverses the maneuvering shaft and penetrates into the tube, said rod including equidistant catches with a length corresponding to that of the screws, a trigger which can be maneuvered manually in a backward and forward movement parallel to the axis of the tube and which is equipped with a stud intended to be inserted in one of the catches of the rod, making it possible to advance said rod, upon displacement of said trigger, toward the free end of the tube, and with a retractable stud allowing the rod to be blocked upon the return of the trigger.

In a first embodiment of the invention, the means for rotationally blocking a screw in the screwing position is obtained by adaptation to the shape of the heads of the screws the internal cross section of the tube containing the aligned screws, which is polygonal.

In a second embodiment of the invention, the means for rotationally blocking a screw in the screwing position is a stud which is integral with the inner wall of the tube, at its free end, between two of the longitudinal slots of said free end, and which is intended to engage in a recess formed longitudinally in the head of said screw, it being possible for each of the heads of the screws contained in the tube to comprise several recesses.

In order to facilitate the surgeon's work, the shaft can advantageously be equipped with a device for illuminating the operating area, and with its supply lines.

The advantages and the characteristics of the present invention will emerge more clearly from the description which follows and in which reference is made to the attached drawing, it being understood that this description is by no means of a limiting nature vis-à-vis the invention.

BRIEF DESCRIPTION OF THE DRAWING FIGURES

In the attached drawing:

FIG. 2 represents a partial longitudinal cross section through this same screwing device according to the invention.

DESCRIPTION OF THE PREFERRED EMBODIMENTS

Figure 1:
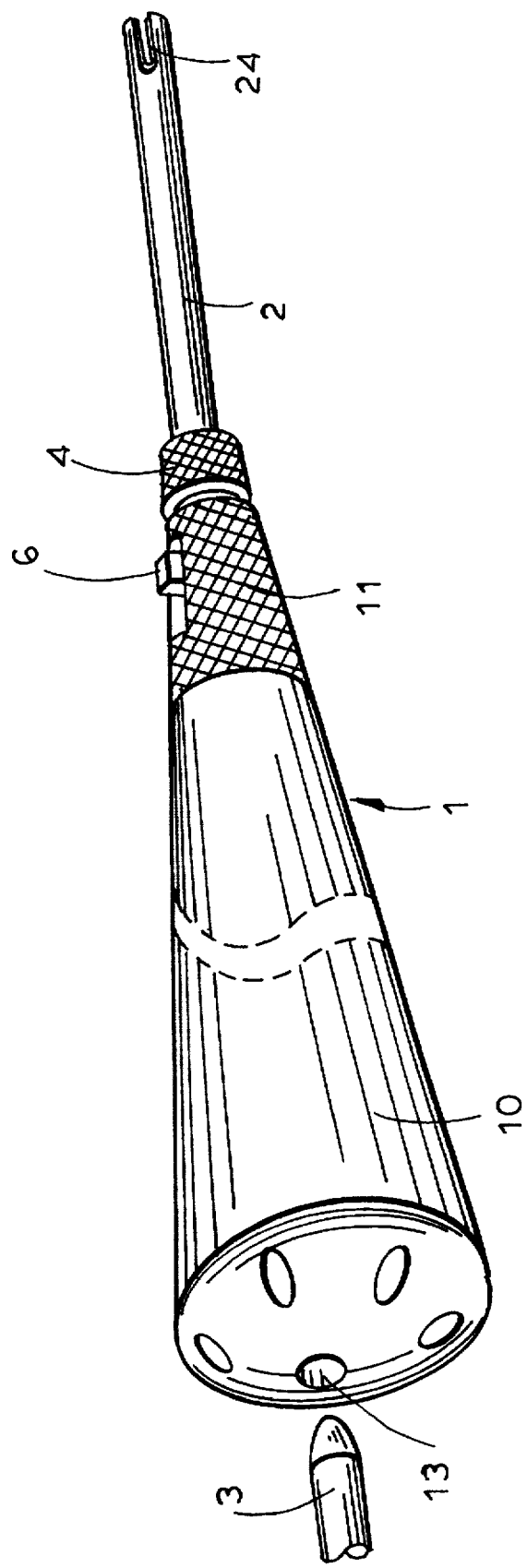
FIG. 1 represents a perspective view of the device according to the invention.

Referring to these figures, it can be seen that in a preferred embodiment the screwing device according to the invention comprises a shaft 1 formed with an end piece 10 made of silicone for the maneuvering of the screwing device, and continued axially via a piece 11 accommodating, in its front part, a seat 12 intended to axially receive one of the ends of a metal tube 2 which is blocked in the seat 12 by means of a locking ring 4 which screws onto the front end of the piece 11 around the seat 12 and which includes a channel 40 narrowing rearward so as to form a channel 41 of smaller diameter. The locking is obtained by screwing the locking ring 4 toward the front of the shaft 1, the clamping with the tube 2 then being effected by virtue of locking balls 26 which are arranged in a peripheral groove 27 formed at one of the ends of the tube 2, bearing against the wall of the channel of smaller diameter 41 of the locking ring 4. Two slots 24 are formed longitudinally at the free end of the tube 2.

It can also be seen that the shaft 1 includes a channel 13 traversed by a rod 3 which is intended to thrust screws 5, aligned in the channel 20 of the tube 2, by virtue of a conical centering hole 50 formed in each of the screw heads 51. The rod 3 has a conical end 32 and includes catches 30 situated at an equal distance from one another, each catch 30 being of frustoconical shape 31.

It can additionally be seen that the first screw 52, the threaded part of which protrudes from the free end of the tube 2, is blocked in the screwing position by two rings 22 projecting from the inner wall of the tube 2 at its free end, preventing the first screw 52 both from leaving the tube 2 and also from falling back into the tube 2 during screwing into, for example, an osteotomy plate during maxillofacial surgery.

The screw 52 in the screwing position is driven in rotation with the aid of the tube 2 which has a polygonal internal cross section adapted to the shape of the heads of the screws 5 which it contains. However, the rotation of the screw 52 can also be achieved with the aid of a stud which is integral with the inner wall of the tube 2 at its free end, between the two longitudinal slots 24 formed in said free end, and which is intended to engage in a recess formed longitudinally in the head of said screw 52, in such a way as to drive it in rotation during the rotation of the tube 2.

In the case where a stud is not provided at the free end for limiting the screwing torque, the device can include a torque limiter of a known type situated at the junction between the tube 2 and the maneuvering shaft 1. It will be possible for the torque limiter to be combined with graduations on the locking ring for adjusting the torque limitation for each type of screw, it being possible for each head of the screws 5 contained in the tube to comprise several recesses.

The slots 24, which can be seen in FIG. 1, permit deformation of the wall of the free end of the tube 2, on which wall the rings 22 are made integral, and this makes it easier, on the one hand, to place the screws 5 in the screwing position with the aid of the rod 3 and makes it possible, on the other hand, to limit the clamping torque of the screw 5 which is situated in the screwing position and to release the latter.

It can also be seen in FIG. 2 that a trigger 6, which is movable in translation in an aperture 25 formed in the piece 11, includes a stud 60 inserted in one of the catches 30 of the rod 3. The insertion of the stud 60 is effected during the rearward displacement of the pusher 6 in the aperture 25. A nonreturn stud 7, whose end is beveled, with an inclination substantially equal to that of the frustoconical part 31, retractable by means of a spring 70, is inserted in a catch 30, blocking the rod 3 in terms of rearward displacement. With the beveled part of the stud 7 permitting the passage of the rod 3, the forward displacement of the pusher 6 permits the advance of the rod 3, by a distance substantially equal to that separating two catches 30 and to the length of the screws 5, the effect of this being that after the removal of the screw in the screwing position 52, the following screw is brought into position for the purpose of renewed screwing.

The device according to the invention is intended particularly, although not exclusively, for use in the field of bone surgery, and its principal aim is to facilitate the surgeon's work by affording him or her the possibility of having, on the operating instrument, a plurality of screws which are immediately available, and this in the certainty that it will not be possible to exceed the clamping torque envisaged for the type of screws being used.

We claim:

1. Screwing device which comprises a tube (2) which encloses axially aligned screws and a maneuvering shaft, said tube having a free end with means for blocking the head of a screw and allowing only a threaded part of said screw to protrude in a screwing position and for blocking the screw against rearward and forward displacement, axial thrust means for bringing said screw (5) into the screwing position and which can be maneuvered by the user; means for rotationally blocking the screw in the screwing position; said tube also comprising, at said free end, at least two longitudinal slots which confer on said free end transverse elasticity for preventing the screw brought into the screwing position from being driven in rotation when a limit torque is reached.

2. Device according to claim 1, wherein the means for blocking a screw in the screwing position comprises two annular and coaxial projections which project from the inner wall of the free end of the tube and are situated at a short distance from one another, and between which the head of the screw takes up position.

3. Device according to claim 1, wherein the thrust means for the screws (5) in the tube is a rod which axially traverses the maneuvering shaft and penetrates into the tube, the rod including equidistant catches with a length corresponding to that of the screws, a trigger which can be maneuvered manually in a backward and forward movement parallel to the axis of the tube, the trigger being equipped with a stud intended to be inserted in one of the catches (30) of the rod, making it possible to advance the rod upon displacement of said trigger toward the free end of the tube and a retractable stud allowing the rod to be blocked upon the return of the trigger (6).

4. Device according to claim 1, wherein the means for rotationally blocking a screw in the screwing position comprises the tube containing the aligned screws having a polygonal internal cross section adapted to the shape of the heads of said screws.

* * * * *